United States Patent [19]

Adams

[11] Patent Number: 4,574,151

[45] Date of Patent: Mar. 4, 1986

[54] AMINE SALTS AND PRODUCTS CONTAINING THEM

[75] Inventor: Brian W. Adams, Newtown Abbey, Northern Ireland

[73] Assignee: Peter Robin Broughton Lawrence, London, England

[21] Appl. No.: 522,413

[22] Filed: Aug. 11, 1983

[30] Foreign Application Priority Data

Aug. 20, 1982 [GB] United Kingdom ............... 8223983

[51] Int. Cl.[4] .............................................. C08B 15/06
[52] U.S. Cl. ..................................... 536/31; 536/30; 536/32; 536/43
[58] Field of Search ................... 536/30, 31, 32, 43; 424/264; 514/343

[56] References Cited

U.S. PATENT DOCUMENTS

| | | | |
|---|---|---|---|
| 3,071,509 | 1/1963 | O'Neill | 424/264 |
| 3,368,567 | 2/1968 | Speer | 424/264 |
| 3,870,794 | 3/1975 | Hutchinson et al. | 424/264 |
| 4,236,532 | 12/1980 | Schweizer et al. | 131/365 |
| 4,464,434 | 8/1984 | Davis | 424/264 |

FOREIGN PATENT DOCUMENTS

| | | | |
|---|---|---|---|
| 4470/26 | of 1928 | Australia | 424/264 |
| 114249 | 12/1941 | Australia | 424/264 |
| 1391614 | 4/1975 | United Kingdom . | |

*Primary Examiner*—Ronald W. Griffin
*Attorney, Agent, or Firm*—Paul & Paul

[57] ABSTRACT

A water soluble salt is formed between an alkaloid and a polymeric acid and contains at least 40% by weight of the alkaloid. The alkaloid is generally nicotine and the polymeric acid is generally a polysaccharide that has been modified by carboxyalkyation or reaction with a polybasic acid. The resultant salt can be formed as a film, a particulate solid or as an aqueous solution and the solution can be used for printing.

12 Claims, No Drawings

AMINE SALTS AND PRODUCTS CONTAINING THEM

Alkaloids have various uses but tend to suffer from the disadvantage that it is difficult to provide prolonged and controlled availability. They are bases and so salts with simple acids can be formed but they are generally very soluble and readily washed off surfaces. Some salts with cross-linked cation exchange resins are known, but are insoluble and so are substantially inactive and are difficult to apply. For instance, nicotine (which is useful as an insecticide) is very volatile and its salts with simple acids are very soluble.

In British Patent Specification No. 1,391,614 it is proposed to form nicotine pectinate or nicotine alginate and to incorporate this in smoking products. Typically a slurry is formed of tobacco winnowings and/or offal and nicotine pectinate or alginate is added to the slurry, either as powder or as solution, and the slurry is cast into a sheet. The nicotine contents of the nicotine alginates and nicotine pectinates quoted in that specification range between 20% and 31.5%, by weight based on the weight of the salt. The nicotine content of the nicotine alginate or nicotine pectinate solutions quoted in the specification range from 1.5 to 1.8% by weight of the solution.

In U.S. Pat. No. 4,236,532 there are disclosed smoking rods in which the wrapper is screen printed with dots of an ink containing a salt of nicotine, usually nicotine hydrogen tartrate. The salt is first made up into a printing ink having rheological properties suitable for screen printing by incorporating silicon dioxide and carboxymethyl cellulose into a solution of nicotine hydrogen tartrate. The nicotine content of the various simple nicotine salts mentioned in that specification (for instance nicotine hydrogen tartrate) cannot exceed around 30% by weight as it is necessary to incorporate significant amounts of the tartrate or other acidic moiety into the smoking product in order to stabilise the desired amount of nicotine. The presence of significant amounts of volatile acids of this type can be undesirable, especially in smoking rods.

Prior to the present invention it was therefore accepted as inevitable that most soluble salts of nicotine or other alkaloid are extremely soluble, most of the salts are formed with volatile acids and all of the salts contain not more than about 30% by weight nicotine or other alkaloid.

The present invention is based in part on our realisation that these limitations are both undesirable and avoidable. By the invention it is now possible to obtain water soluble salts in which the acid component is not highly volatile and in which the alkaloid component can provide a much higher proportion, by weight, of the salt than has previously been possible.

According to the invention a water soluble salt is formed between an alkaloid and a polymeric acid and contains at least 40%, and preferably 45 to 60%, by weight alkaloid.

The alkaloid may be any alkaloid that will form a salt with the polymeric acid. Preferred alkaloids are nicotine, anabasine and nornicotine.

The alkaloids may be compounds that can occur naturally or they may be analogues or derivatives that have to be synthesised. Nicotine is the most preferred alkaloid.

A polymeric acid is a polymer containing a recurring moiety that includes at least one acid group. The polymeric acid can therefore be any such polymer which is capable of forming a water soluble salt having the desired content of alkaloid. By saying that the salt is water soluble we mean that it forms a true solution or a colloidal solution in water or in an aqueous organic solvent.

The acidic groups of the polymeric acid are generally carboxylic groups but other salt-forming acid groups that may be present include phosphate, sulphate, borate and sulphonate.

The polymeric acid may be naturally occurring or synthetic. If naturally occurring, it is generally modified so as to increase its content of acidic groups, so as to permit the desired high nicotine content in the salt.

Preferably it is a polysaccharide that has been modified by increasing its acidic content so that the average number of acid groups per saccharide unit is increased by at least 0.1 and preferably by at least 1. The preferred way of increasing its acidic content is by carboxyalkylation. The alkyl group of the carboxyalkyl generally contains 1 to 6, preferably 1 to 4, carbon atoms, e.g. methyl or butyl. Another way of increasing acidity is by reaction with a polybasic acid (or a salt thereof followed by acidification if necessary). Suitable polybasic acids include phosphoric, boric, sulphuric, tartaric and malonic acids. The polybasic acid is usually dibasic or tribasic.

The polysaccharide may be formed from 5 membered rings but preferably is formed from 6 membered rings. Suitable polysaccharides include alginic acid and pectic acid that have been modified to increase their acid content, generally by carboxyalkylation or by reaction with polybasic acid, to increase its degree of acidic substitution by at least 0.1 (i.e. to increase the average number of acid groups per saccharide unit by at least 0.1). Generally the degree of substitution is increased by between 0.8 or 1 and 2. Suitable polysaccharides therefore include borated, carboxymethylated, carboxybutylated or phosphated alginic or pectic acid having degrees of acidic substitution increased by 0.1 to 2, preferably between 0.8 or 1 and 2.

The preferred polysaccharide is cellulose that has been modified by having a degree of acidic substitution of at least 0.8 or 1 and up to 3. Any hydroxyl groups in the cellulose or other polysaccharide remaining after the acidic substitution may be present as free hydroxy groups or may be present as ether or ester groups formed with, for instance, $C_{1-6}$ alkyl or hydroxyalkyl groups such as methyl, ethyl, hydroxyethyl and hydroxypropyl.

Preferred cellulosic compounds are carboxyalkylated cellulose where alkyl is preferably methyl or butyl and cellulose phosphate, each having degrees of acidic substitution of at least 0.8 or 1 and up to 3, and the corresponding compounds in which the hydroxy groups in the ring are converted to ethers by alkyl (usually methyl or ethyl) or hydroxyalkyl (usually hydroxyethyl or hydroxypropyl) groups.

The polysaccharide will contain at least 3 units and normally more, for instance at least 40 and often at least 100 units. It is generally desirable that it does not contain more than 10,000 units and normally it contains considerably less than this, typically below 5,000 units, since the higher molecular weights result in the products forming very viscous solutions that can be difficult to handle. Preferably the polysaccharide contains less than 1,000 units and best results are often obtained with polysaccharides containing from 50 to 300 units.

Preferred synthetic polymers that may be used as the polymeric acids in the invention include polymers of acrylic, methacrylic, and maleic acids. The polymers preferably contain from 500 to 4,000 recurring units and thus may have molecular weights ranging from, for instance, 10,000 to 1 million but again the lower molecular weights, typically 10,000 to 100,000 are often preferred. For some purposes other polymeric acids may be used, for instance polymers of butadiene carboxylic acid and linear styrene sulphonic acid.

The polymeric acids are known materials or can be made by methods analogous to well known methods. Alkaloid salts of the polymeric acids can be made by combining the alkaloid with the polymeric acid while dissolved in a polar solvent. If the polymeric acid is initially provided in the form of an alkali metal salt (for instance sodium carboxymethyl cellulose) it is preferably converted to its free acid form before being mixed with the alkaloid. This conversion may be conducted in known manner by treatment with mineral acid but we have found that the best results, and the highest conversion and consequently the highest eventual alkaloid content, is obtainable if the conversion is conducted by ion exchange with a cationic exchange resin.

The customary way of isolating an amine salt is to crystallise or precipitate it from the solution in which it is formed and to separate the precipitate by filtration. For instance upon addition of nicotine to an aqueous solution of polyacrylic acid or other synthetic polymer a precipitate of polyacrylic alkaloid salt forms on standing and can be separated by filtration.

A salt can also be formed in similar manner when a polysaccharide acid is used in place of the polyacrylic acid but the yield of salt, and in particular the alkaloid content of the salt, is liable to be rather low. We have surprisingly found that improved results can be obtained if a solution is formed of the polysaccharide alkaloid salt in a polar solvent, by dissolving the saccharide and the alkaloid in the solvent and this solution is then evaporated to remove solvent, to give a concentration of the salt of at least 30% by weight and generally at least 30% to 50% by weight. If the salt is required in the form of a solid this is best obtained by removing substantially all the solvent by evaporation, although a useful product may also be obtained by crystallisation or precipitation from a concentrated solution obtained by evaporation. For some purposes, e.g. as printing inks or casting solutions, the concentrated solutions may be used without separation of the solid salt.

Evaporation may be by conventional methods, e.g. by distillation (preferably under reduced pressure) or by spray drying.

The solvent is preferably water or an organic solvent such as methanol or ethanol or other protonic solvent.

The novel salts are useful as a stable source providing a high content of readily available alkaloid that may be used for its known uses for instance as insecticidal products when the alkaloid is anabasine or nicotine, or smoking products when the alkaloid is nicotine.

Novel compositions according to the invention comprise the polymeric acid salt and a carrier. The composition may be a flowable composition, for instance a powder or liquid, in which event the carrier may be an inert powder or inert liquid in which the salt is dissolved or dispersed.

Flowable compositions may be sprayed, painted, dusted or drenched onto the area to be treated, in conventional manner. Liquid compositions may be made by dissolving solid salt (made for instance by spray drying or otherwise evaporating a solution of salt) or by partial evaporation of a solution of the salt for controlled release at a chosen location.

A preferred liquid composition is a printing ink comprising a liquid vehicle that contains the salt and that is preferably substantially free of other organic thickeners. A printed product according to the invention comprises paper or other sheet substrate carrying a pattern of deposits of the salt, the pattern having been applied by printing the described printing ink using conventional printing techniques such as screen or gravure printing. Preferably, the pattern is made up of dots. The inks, and therefore the printed deposits may contain other additives. Such additives may be present to provide beneficial properties to the final product, for instance they may be colouring agents or smoking additives such as flavourants, smoke producers and burn modifiers. Apart from such optional additives the ink preferably consists substantially only of the aqueous solution of the salt and in particular the ink preferably contains no additional alkaloid, binder and viscosity regulator. Appropriate control of the viscosity and other characteristics of the ink can be achieved by appropriate selection of the concentration of the salt in the solution, the choice of the particular salt and, in particular, the molecular weight of the polymeric acid component of the salt. The ink will generally have a viscosity in the range 10 poise up to 500 poise, depending upon the method of printing. For instance when the ink is to be applied by gravure printing the viscosity is generally in the range 20 to 200, most preferably 50 to 150 poise, whilst for screen printing the viscosity is preferably in the range 100 to 450 poise, most preferably 150 to 400 poise. The polysaccharide acids are preferred for use in printing inks.

The salt can be provided in the form of a film. This may be a self-supporting film of the salt, having been made by casting or other convenient film forming techniques. Alternatively, it may be supported on or reinforced by other material. For instance, an aqueous or ethanolic solution or gel of the salt may be sprayed or otherwise deposited on a fibrous mass or on a fibrous sheet and then dried so as to act as both a source of alkaloid and a stiffener for the fibrous mass or sheet.

The salt will generally have an activity similar to that of the alkaloid. When the alkaloid is insecticidally active, (e.g. nicotine or anabasine) these products may be used as insecticidal products. The invention also includes smoking products that include the nicotine salts. For instance, a printed sheet, made as described above, may be used as a wrapper for a smoking rod. Particulate salt may be incorporated particular advantage that the printing ink can contain a high nicotine content, can be free of volatile acid component, and does not need to contain viscosity adjusting agents. These valuable properties are unique to the salts of the invention and are not possessed by the nicotine pectinate, alginate or tartrate salts that are disclosed in the aforementioned Patent Specifications.

The following are Examples of the invention.

EXAMPLE 1

30 g sodium carboxymethyl cellulose having a degree of substitution of 1.2 and an average degree of polymerisation of around 1100 was gelled in 300 mls water. 50 g of a cation exchange resin sold under the trade name Duolite 225 in the acid form was mixed into the solution and the mixture left for 1 hour. The resulting gel was filtered through a muslin cloth to remove the ion exchange resin and was a solution of the acid form of carboxymethyl cellulose.

30 g nicotine was added to the filtrate and the mixture stirred well. Water was removed from the solution by distillation and reduced pressure using a rotary evaporator. Evaporation was continued until the solution had become sufficiently concentrated that it had a consistency suitable for printing. At this stage its solid content was about 33% by weight and analysis showed that its nicotine content was about 17% by weight.

Its viscosity was 130 poise.

The solution was then printed by gravure onto one surface of a conventional cigarette paper and the dots were dried by exposure to air at 100 degree C. for 1 minute. The dried dots had a diameter of about 1 mm, a height of about 75μ and the separation between their centres was substantially uniform and was about 2 mm. The dry weight of the printed material was about 3 mg/cm$^2$ and analysis showed that the dots consisted of a nicotine salt of carboxymethyl cellulose containing about 50% by weight nicotine. Nicotine could not be removed from the deposits by washing with hexane or diethyl ether.

EXAMPLE 2

A solution of the acid form of carboxymethyl cellulose was formed and nicotine was added to it, all as in Example 1. The water was then removed entirely from the solution by distillation and reduced pressure using a rotary evaporator, so as to produce a solid deposit in the evaporator. This deposit was then further dried by heating to 60° C. for 1 hour to give 57 g product. Analysis by GLC showed that the product contained about 50% by weight nicotine and consisted of the nicotine salt of carboxymethyl cellulose. Washing by hexane or by diethyl ether removed no nicotine, showing that all the nicotine was bound into the salt. The product appeared indistinguishable from the dried deposits formed in Example 1.

EXAMPLE 3

A slurry of alginic acid (17.7 g) in 40 ml of water was formed and boric acid (3.1 g) stirred into the gel until a homogeneous suspension was obtained. Nicotine (24.4 g) was added and the stirred mixture left for 30 minutes. The suspension obtained contained 53% solids and was suitable for printing. Removal of the water by rotary evaporating produced a solid containing 55.1% nicotine. Washing with hexane or with diethyl ether removed no nicotine, showing that all the nicotine was bound into the salt.

EXAMPLE 4

Carboxymethyl cellulose having a degree of substitution of 1.2 and a degree of polymerisation of 1100 was prepared by reaction of sodium carboxymethyl cellulose with hydrochloric acid in a mixture of methanol (70%) and water (30%). 237 g of this carboxymethyl cellulose having a degree of substitution of 1.2 and a degree of polymerisation of 1100 was slurried in 2370 ml of water. 194 g of free base nicotine was added to the slurry under conditions of high speed stirring; a homogeneous gel was formed which was suitable for use as a printing composition. Evaporation of solvent from the gel at 75° C. gave a solid material containing 45% by weight of nicotine.

EXAMPLE 5

288 g of carboxybutyl cellulose having a degree of substitution of 1.2 and a degree of polymerisation of less than 1100 was slurried in 2500 ml of water. 200 g of free base nicotine was added to the slurried mixture and the stirring continued until a homogeneous gel was formed. The gel was suitable for use as a printing composition; evaporation of solvent gave a solid containing 40% by weight of free base nicotine.

EXAMPLE 6

50 g of carboxymethyl hydroxypropyl cellulose prepared by carboxymethylation of hydroxypropyl cellulose having a degree of polymerisation of less than 500 was dispersed in 500 ml of water. 36 g of free base nicotine was added to the stirred dispersion; a homogeneous gel suitable for use as a printing composition was obtained. Evaporation of solvent at 75° C. gave a solid containing 41% nicotine.

EXAMPLE 7

50 g of cellulose phosphate having a degree of substitution of 0.9 and a degree of polymerisation of less than 1000 was dispersed in 500 ml of water. 38 g of free base nicotine was added to the stirred dispersion and stirring continued until a homogeneous gel was formed. The gel is suitable for use as a printing composition. Evaporation of solvent at 75° C. gave a solid containing 43% by weight of nicotine.

EXAMPLE 8

915 g of alginic acid phosphate ester having a degree of substitution of 0.9 and a degree of polymerisation of 1000 was slurried in 1950 ml of water. 215 g of free base nicotine was added to the slurry under conditions of high speed stirring; a homogeneous gel was formed which was suitable for use as a printing composition. Evaporation of the solvent at 75° C. gave a solid material containing 53% nicotine.

EXAMPLE 9

175 g of alginic acid (Alginate Industries, LDB grade) was slurried in 1450 ml of water and 180 g of free base nicotine added to the slurried suspension. 31 g of ortho boric acid dissolved in 600 ml of water was added to the gelled solution causing the viscosity of the gel to increase markedly. The gelled product is suitable for use as a printing composition; evaporation of solvent gave a solid containing 50% by weight of nicotine.

EXAMPLE 10

19.5 g of alginic acid phosphate ester having a degree of substitution of 0.9 and a degree of polymerisation of 1000 is slurried with 200 ml of water. 21.5 g of anabasine, 1-2(3-pyridyl)-piperidine, is added and the mixture stirred well. A homogeneous gel is formed which is suitable for use as a printing composition. Printed deposits contain 51% anabasine.

EXAMPLE 11

19.5 g of alginic acid phosphate ester having a degree of substitution of 0.9 and a degree of polymerisation of 1000 is slurried i- 200 mls of water. 19.5 g of nornicotine, 1-3(2-pyrrolidyl) pyridine is added and the mixture stirred well. A homogeneous gel is formed which is suitable for use in a printing composition. Printed deposits contain 48% nornicotine.

EXAMPLE 12

73 g of polyacrylic acid having a degree of polymerisation of 3000 is dispersed in 1 liter of water and 73 g of free base nicotine added to the stirred mixture. Evaporation of solvent under reduced pressure gives a brittle hygroscopic solid which contains 50% by weight of nicotine. The nicotine cannot be removed by repeated washing with hexane.

Instead of isolating the solid salt in each of Examples 4 to 12 the homogeneous gel can be used in other ways. For instance, the gel as formed, or after partial evaporation, may be spread over a smooth surface, for instance a glass plate, and allowed to air dry. This results in the formation of a coherent film consisting of the salt and having a nicotine content corresponding to the nicotine content quoted in Examples 4 to 12.

The homogeneous gel solutions can also be used as printing inks either as formed or after partial evaporation. Thus, they may be printed in the same manner as in Examples 1 to 3.

I claim:

1. A water soluble salt formed between a naturally occurring polysaccharide polymeric acid modified to increase the average number of acid groups per saccharide unit and at least 40% (by weight of the salt) of an alkaloid.

2. A salt according to claim 1, in which the alkaloid is selected from nicotine and anabasine and nornicotine.

3. A salt according to claim 1, in which the alkaloid is nicotine.

4. A salt according to claim 1, in which the amount of alkaloid is 45 to 60% by weight of the salt.

5. A salt according to claim 1, in which the polymeric acid is a polysaccharide that has been modified to increase the average number of acid groups per saccharide unit by at least 0.1 by carboxyalkylation or by reaction with a polybasic acid.

6. A salt according to claim 5, in which the polysaccharide is alginic acid or pectic acid which has been modified to increase its degree of acidic substitution by 0.1 to 2.

7. A salt according to claim 5, in which the polysaccharide is cellulose and has a degree of acidic substitution of 0.1 to 3.

8. A salt according to claim 1, in which the polymeric acid is selected from phosphate esters of alginic acid and pectic acid and borate esters of alginic acid and pectic acid.

9. A salt according to claim 1, in which the polymeric acid is carboxyalkyl cellulose having a degree of acidic substitution of 1 to 3 and wherein each alkyl group contains 1 to 4 carbon atoms.

10. The salt according to claim 9 wherein the hydroxyl groups in the cellulose are substituted by akyl or hydroxyalkyl groups containing 1 to 6 carbon atoms.

11. A salt according to claim 1, in which the polymeric acid is selected from carboxymethyl cellulose, carboxybutyl cellulose, cellulose phosphate ester and cellulose borate ester.

12. A salt according to claim 1, in which the polymeric acid is the polysaccharide cellulose that has a degree of acidic substitution of 0.1 to 3 and the alkaloid is nicotine.

* * * * *